(12) United States Patent
Frances

(10) Patent No.: US 7,247,660 B2
(45) Date of Patent: *Jul. 24, 2007

(54) DENTAL COMPOSITION BASED ON SILICONE CROSSLINKABLE BY CATION PROCESS

(75) Inventor: Jean-Marc Frances, Meyzieu (FR)

(73) Assignee: Rhodia Chimie, Aubervilliers (FR)

( * ) Notice: Subject to any disclaimer, the term of this patent is extended or adjusted under 35 U.S.C. 154(b) by 313 days.

This patent is subject to a terminal disclaimer.

(21) Appl. No.: 10/781,064

(22) Filed: Feb. 18, 2004

(65) Prior Publication Data

US 2004/0171717 A1 Sep. 2, 2004

Related U.S. Application Data

(62) Division of application No. 09/806,629, filed on Jun. 25, 2001, now Pat. No. 6,747,071.

(51) Int. Cl.
*A61C 13/00* (2006.01)

(52) U.S. Cl. .......................... 523/113; 522/22; 522/26; 522/27; 522/28; 522/49; 522/67; 522/99; 522/170; 522/908

(58) Field of Classification Search ................. None
See application file for complete search history.

(56) References Cited

U.S. PATENT DOCUMENTS

| | | | |
|---|---|---|---|
| 5,468,902 A | 11/1995 | Castellanos | 556/7 |
| 5,703,137 A | 12/1997 | Priou | 522/148 |
| 6,025,406 A | 2/2000 | Oxman | 522/14 |
| 6,245,828 B1 | 6/2001 | Weinmann | 433/228 |
| 2005/0059752 A1* | 3/2005 | Frances | 523/113 |

* cited by examiner

Primary Examiner—Marc S. Zimmer
(74) Attorney, Agent, or Firm—Buchanan, Ingersoll & Rooney, PC

(57) ABSTRACT

The invention concerns dental compositions. Said composition comprises (1) a silicone crosslinkable and/or polymerizable by cation process; (2) an efficient amount of at least an initiator such as onium borate; (3) at least a photosensitizer ; and (4) a dental filler present in the composition in a proportion of at least 10 wt. % relative to the composition total weight. Said dental compositions are useful for making dental prostheses or for dental restoration.

6 Claims, No Drawings

DENTAL COMPOSITION BASED ON SILICONE CROSSLINKABLE BY CATION PROCESS

This application is a division of U.S. application Ser. No. 09/806,629, filed on Jun. 25, 2001 now U.S. Pat. No 6,747,071.

The field of the invention is that of dental compositions. More precisely, the dental compositions used in the context of the present invention can be used for producing dental prostheses and for dental restoration.

Up until now, to produce dental compositions for the preparation of dental prostheses or of dental restoration materials, it is possible to use resins based on photopolymerizable acrylates. These ready-to-formulate products exhibit however upon use problems of irritation and potential problems of toxicity.

In addition, these products have the major disadvantage of causing high volume shrinkage during their polymerization, which makes their use complex and difficult for the production of dental prostheses or of dental restoration materials. Problems of attachment due to the volume shrinkage or to the lack of adherence of the polymers used are in particular observed.

The object of the present invention is to provide novel dental compositions which do not exhibit the disadvantages of the prior art. These novel dental compositions, which are polymerizable and/or crosslinkable in an oral environment, have markedly improved qualities, in particular as regards the very marked reduction in the phenomenon of shrinkage of the dental compositions used for the production of dental prostheses or of dental restoration materials.

The polymerizable and/or crosslinkable dental composition according to the invention comprises:

(1) at least one crosslinkable and/or polymerizable silicone oligomer or polymer which is liquid at room temperature or which is heat-meltable at a temperature of less than 100° C., and which comprises:

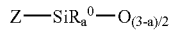

$$Z-SiR_a^0-O_{(3-a)/2}$$

in which:
a=0, 1 or 2,
$R^0$, identical or different, represents an alkyl, cycloalkyl, aryl, vinyl, hydrogeno or alkoxy radical, preferably a $C_1$-$C_6$ lower alkyl,
Z, identical or different, is an organic substituent comprising at least one reactive epoxy, and/or alkenyl ether and/or oxetane and/or dioxolane and/or carbonate functional group, and preferably Z being an organic substituent comprising at least one reactive epoxy and/or dioxolane functional group,
and at least two silicon atoms, (2) an effective quantity of at least one borate-type photoinitiator, (3) at least one aromatic hydrocarbon photosensitizer with one or more aromatic nuclei which are substituted or not, having a residual light absorption of between 200 and 500 nm, (4) and at least one dental filler present in a proportion of at least 10% by weight relative to the total weight of the composition.

According to a first advantageous variant of the present invention, the dental composition is polymerizable and/or crosslinkable under activation by the thermal route and/or by the photochemical route.

In general, the photochemical activation is carried out under UV radiation. More particularly, UV radiation having a wavelength of the order of 200 to 500 nm is used for the production of dental prostheses and UV-visible radiation having a wavelength greater than 400 nm for the production of restoration materials; A wavelength greater than 400 nm allows crosslinking and/or polymerization in an oral environment.

The silicone polymer or oligomer (1) has the advantage, compared with organic resins which are crosslinked by the cationic route, of being transparent to UV-visible light and therefore its use makes it possible to obtain materials which are very thick and whose photocrosslinking occurs in a short time.

The reactive functional groups Z of the silicone polymer or oligomer (1) may be highly varied. However, particularly advantageous dental compositions are obtained when the silicone oligomer or polymer (1) comprises at least one (FS) unit in which Z represents an organic substituent Z1 comprising at least one reactive epoxy, and/or dioxolane functional group, and preferably at least one reactive epoxy functional group.

According to two advantageous alternatives of the present invention, the silicone oligomer or polymer (1) with at least one reactive epoxy and/or dioxolane functional group Z1, and preferably at least one reactive epoxy functional group may:

(i) either comprise only this (these) type(s) of reactive functional group(s) Z1, (ii) or comprise other reactive functional groups Z such as the reactive alkenyl ether, oxetane and/or carbonate functional groups Z2.

In the case of the first alternative (i), the dental composition may also comprise other silicone oligomers and/or polymers comprising other reactive functional groups Z2 such as alkenyl ether, oxetane and/or carbonate functional groups and optionally reactive functional groups Z1.

By way of examples of reactive functional groups Z, these may in particular be chosen from the following radicals:

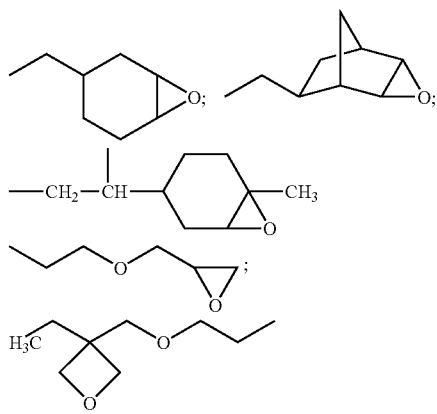

-continued
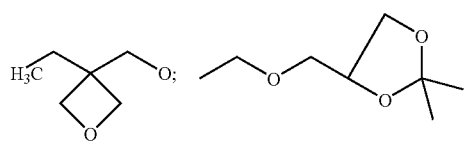
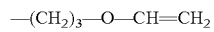
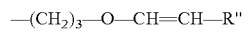
with R″ representing a linear or branched $C_1$-$C_6$ alkyl radical.
According to a second advantageous variant of the present invention, the silicone polymer or oligomer consists of at least one silicone having the following average formula:
a)
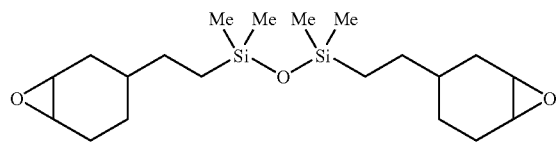
b)
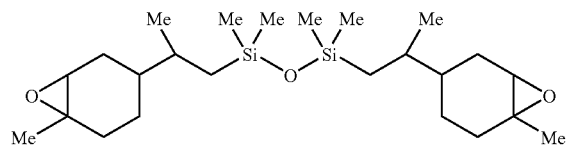
c)
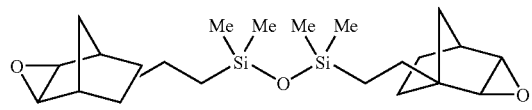
d)
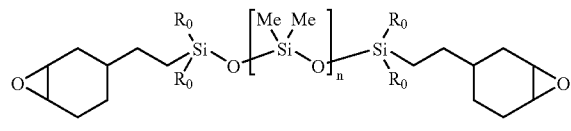
(n < 1000)
e)
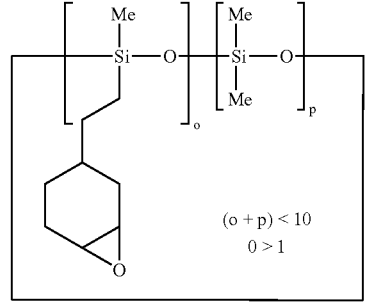
f)
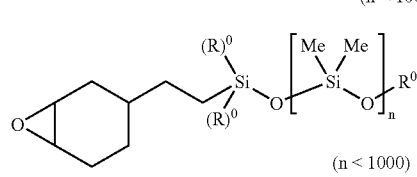
(n < 1000)
g)
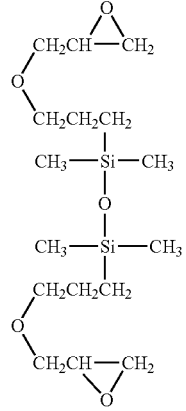
(o + p) < 10
o > 1
h)
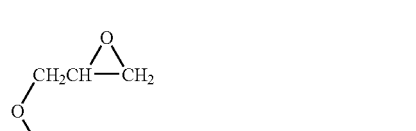
i)
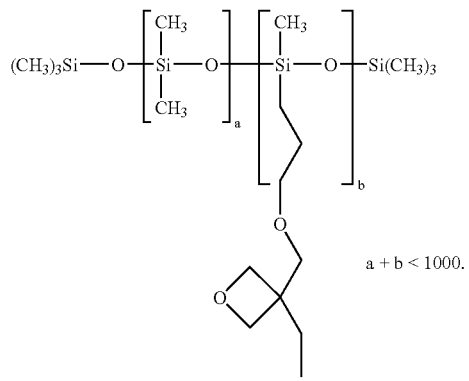
a + b < 1000.

-continued

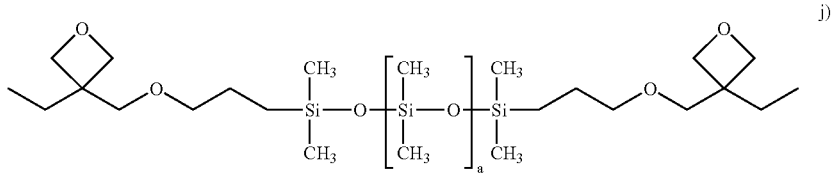
j)

a < 1000.

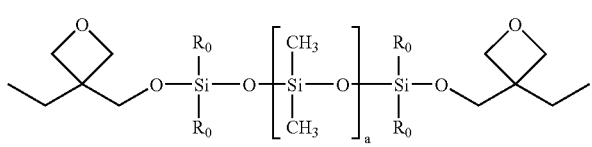
k)

a < 1000.

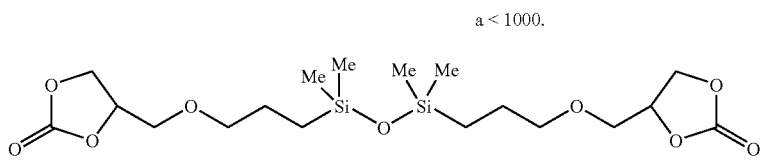
l)

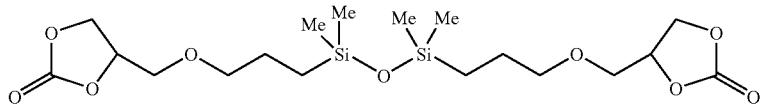
m)

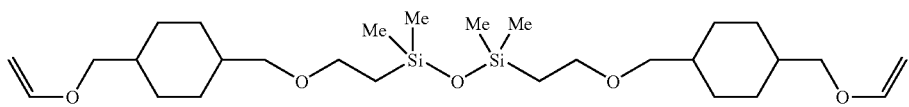
n)

The cationic photoinitiators are chosen from onium borates (taken on their own or as a mixture with each other) of an element of groups 15 to 17 of the Periodic Table [Chem. & Eng. News, vol. 63, No. 5, 26 of 4 Feb. 1985] or of an organometallic complex of an element of groups 4 to 10 of the Periodic Table [same reference].

The cationic entity of the borate is selected from:

(1) the onium salts of formula (I)

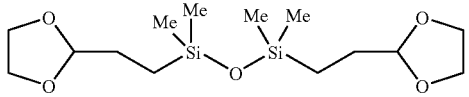  (I)

in which formula:
  A represents an element of groups 15 to 17 such as for example: I, S, Se, P or N,
  $R^1$ represents a carbocyclic or heterocyclic $C_6$-$C_{20}$ aryl radical, it being possible for said heterocyclic radical to contain, as heteroelements, nitrogen or sulfur,
  $R^2$ represents $R^1$ or a linear or branched $C_1$-$C_{30}$ alkyl or alkenyl radical; said radicals $R^1$ and $R^2$ being optionally substituted with a $C_1$-$C_{25}$ alkoxy, $C_1$-$C_{25}$ alkyl, nitro, chloro, bromo, cyano, carboxyl, ester or mercapto group,
  n is an integer ranging from 1 to v+1, v being the valency of the element A,
  m is an integer ranging from 0 to v−1 with n+m =v+1, (2) the oxoisothiochromanium salts described in patent application WO 90/11303, in particular the sulfonium salt of 2-ethyl-4-oxoisothiochromanium or 2-dodecyl-4-oxoisothiochromanium, (3) the sulfonium salts in which the cationic entity comprises:

$3_1$ at least one polysulfonium entity of formula (II.1):

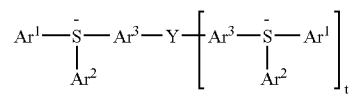

in which:
  the symbols $Ar^1$, which are identical or different, each represent a monovalent phenyl or naphthyl radical, optionally substituted with one or more radicals chosen from: a linear or branched $C_1$-$C_{12}$, preferably $C_1$-$C_{16}$, alkyl radical, a linear or branched $C_1$-$C_{12}$, preferably $C_1$-$C_6$, alkoxy radical, a halogen atom, an —OH group, a —COOH group, an ester group —COO-alkyl where the alkyl portion is a linear or branched $C_1$-$C_{12}$, preferably $C_1$-$C_6$, residue, and a group of formula —$Y^4$—$Ar^2$ where the symbols $y^4$ and $Ar^2$ have the meanings given just below,
  the symbols $Ar^2$, which are identical or different, each represent a monovalent phenyl or naphthyl radical, optionally substituted with one or more radicals chosen from: a linear or branched $C_1$-$C_{12}$, preferably $C_1$-$C_6$, alkyl radical, a linear or branched $C_1$-$C_{12}$, preferably $C_1$-$C_6$, alkoxy radical, a halogen atom, an —OH group, a —COOH group, an ester group —COO-alkyl where the alkyl portion is a linear or branched $C_1$-$C_{12}$, preferably $C_1$-$C_6$, residue,
  the symbols $Ar^3$, which are identical or different, each represent a divalent phenylene or naphthylene radical, optionally substituted with one or more radicals chosen from: a linear or branched $C_1$-$C_{12}$, preferably $C_1$-$C_6$, alkyl radical, a linear or branched $C_1$-$C_{12}$, preferably $C_1$-$C_6$, alkoxy radical, a halogen atom, an —OH group, a —COOH group, an ester group —COO-alkyl where the alkyl portion is a linear or branched $C_1$-$C_{12}$, preferably $C_1$-$C_6$, residue, t is an integer equal to 0 or 1, with the additional conditions according to which:

+ when t=0, the symbol Y is then a monovalent radical $Y^1$ representing the group of formula:

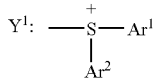

where the symbols $Ar^1$ and $Ar^2$ possess the meanings given above,

+ when t=1:
  ○ on the one hand, the symbol Y is then a divalent radical having the following meanings $Y^2$ to $Y^4$:
  $Y^2$ a group of formula:

where the symbol $Ar^2$ has the meanings given above,
$Y^3$: a single valency bond,
$Y^4$: a divalent residue chosen from: —O—, —S—,

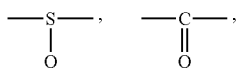

a linear or branched $C_1$-$C_{12}$, preferably $C_1$-$C_6$, alkylene residue and a residue of formula —Si $(CH_3)_2O$—, ○ on the other hand, in the case solely where the symbol Y represents $Y^3$ or $Y^4$, the (terminal) radicals $Ar^1$ and $Ar^2$ possess, in addition to the meanings given above, the possibility of being linked to each other by the residue Y' consisting of $Y'^1$ a single valency bond or of $Y'^2$ a divalent residue chosen from the residues cited in relation to the definition of $Y^4$, which is inserted between the carbon atoms, opposite each other, situated on each aromatic ring at the ortho position with respect to the carbon atom directly linked to the cation $S^+$;

$3_2$ and/or at least one monosulfonium entity possessing a single cationic center $S^+$ per mol of cation and consisting, in most cases, of entity of formula (II.2):

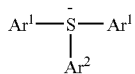

in which $Ar^1$ and $Ar^2$ have the meanings given above in relation to formula (III.1), including the possibility of directly linking to each other only one of the radicals $Ar^1$ to $Ar^2$ in the manner indicated above in relation to the definition of the additional condition in force when t=1 in formula (II), calling into play the residue Y';

(4) the organometallic salts of formula (III):

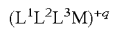

in which formula:
M represents a group 4 to 10 metal, in particular iron, manganese, chromium or cobalt, $L^1$ represents 1 ligand bound to the metal M by $\pi$ electrons, which ligand is chosen from the ligands $\eta^3$-alkyl, $\eta^5$-cyclopendadienyl and $\eta^7$-cycloheptratrienyl and the $\eta^6$-aromatic compounds chosen from the optionally substituted $\eta^6$-benzene ligands and the compounds having from 2 to 4 condensed rings, each ring being capable of contributing to the valency layer of the metal M by 3 to 8 $\pi$ electrons;

$L^2$ represents a ligand bound to the metal M by $\pi$ electrons, which ligand is chosen from the ligands $\eta^7$-cycloheptratrienyl and the $\eta^6$-aromatic compounds chosen from the optionally substituted ligands $\eta^6$-benzene and the compounds having from 2 to 4 condensed rings, each ring being capable of contributing to the valency layer of the metal M by 6 or 7 $\pi$ electrons;

$L^3$ represents from 0 to 3 ligands, which are identical or different, linked to the metal M by $\sigma$ electrons, which ligand(s) is (are) chosen from CO and $NO_2^+$; the total electron charge q of the complex to which $L^1$, $L^2$ and $L^3$ contribute and the ionic charge of the metal M being positive and equal to 1 or 2;

The anionic borate entity has the formula $[BX_aR_b]^-$ in which:
a and b are integers ranging, for a, from 0 to 3 and, for b, from 1 to 4 with a+b=4,
the symbols X represent:
a halogen atom (chlorine, fluorine) with a=0 to 3,
an OH functional group with a=0 to 2,
the symbols R are identical or different and represent:
a phenyl radical substituted with at least one electron-attracting group such as for example $OCF_3$, $CF_3$, $NO_2$, CN, and/or with at least 2 halogen atoms (fluorine most particularly), this being when the cationic entity is an onium of an element of groups 15 to 17,
a phenyl radical substituted with at least one element or one electron-attracting group, in particular a halogen atom (fluorine most particularly), $CF_3$, $OCF_3$, $NO_2$, CN, this being when the cationic entity is an organometallic complex of an element of groups 4 to 10,
an aryl radical containing at least two aromatic nuclei such as for example biphenyl, naphthyl, optionally substituted with at least one electron-attracting group or element, in particular a halogen atom (fluorine most particularly), $OCF_3$, $CF_3$, $NO_2$, CN, regardless of the cationic entity.

Without being limiting, more details are given below as regards the subclasses of onium borate and of borate of organometallic salts more particularly preferred in the context of the use in accordance with the invention.

According to a first preferred variant of the invention, the entity of the anionic borate entity which are most particularly suitable are the following:

| | |
|---|---|
| 1' | $[B(C_6F_5)_4]^-$ |
| 2' | $[(C_6F_5)_2BF_2]^-$ |

-continued

| | |
|---|---|
| 3' | [B(C₆H₄CF₃)₄]⁻ |
| 4' | [B(C₆F₄OCF₃)₄]⁻ |
| 5' | [B(C₆H₃(CF₃)₂)₄]⁻ |
| 6' | [B(C₆H₃F₂)₄]⁻ |
| 7' | [C₆F₅BF₃]⁻ |

According to a second preferred variant of the invention, the onium salts (1) which can be used are described in numerous documents, in particular in patents U.S. Pat. Nos. 4,026,705, 4,032,673, 4,069,056, 4,136,102, 4,173,476. Among these, the following cations will be most particularly preferred:

| | | |
|---|---|---|
| [(Φ)₂I]⁺ | [C₈H₁₇—O-Φ-I-Φ]⁺ | [(Φ-CH₃)₂I]⁺ |
| [C₁₂H₂₅-Φ-I-Φ]⁺ | [(C₈H₁₇—O-Φ)₂I]⁺ | [(C₈H₁₇—O-Φ-I-Φ)]⁺ |
| [(Φ)₃S]⁺ | [(Φ)₂-S-Φ-O—C₈H₁₇]⁺ | [(CH₃-Φ-I-Φ-CH(CH₃)₂]⁺ |
| [Φ-S-Φ-S-(Φ)₂]⁺ | [(C₁₂H₂₅-Φ)₂I]⁺ | [(CH₃-Φ-I-Φ-OC₂H₅]⁺ |

According to a third preferred variant, the organometallic salts (4) which can be used are described in the documents U.S. Pat. Nos. 4,973,722, 4,992,572, EP-A-203 829, EP-A-323 584 and EP-A-354 181. The organometallic salts most readily selected according to the invention are in particular:

(η⁵-cyclopentadienyl)(η⁶-toluene) Fe⁺,
(η⁵-cyclopentadienyl)(η⁶-methyl-1-naphthalene) Fe⁺,
(η⁵-cyclopentadienyl)(η⁶-cumene) Fe⁺,
bis(η⁶-mesitylene) Fe⁺,
bis(η⁶-benzene) Cr⁺.

In agreement with these three preferred variants, the following products may be mentioned by way of examples of photoinitiators of the onium borate type:

| | |
|---|---|
| [(Φ)₂I]⁺,[B(C₆F₅)₄]⁻ | [(C₈H₁₇)—O-Φ-I-Φ]⁺,[B(C₆F₅)₄]⁻ |
| [C₁₂H₂₅-Φ-I-Φ]⁺,[B(C₆F₅)₄]⁻ | [(C₈H₁₇—O-Φ)₂I]⁺,[B(C₆F₅)₄]⁻ |
| [(C₈H₁₇)—O-Φ-I-Φ)]⁺, [B(C₆F₅)₄]⁻ | [(Φ)₃S]⁺, [B(C6F5)₄]⁻ |
| [(Φ)₂S-Φ-O—C₈H₁₇]⁺,[B(C₆H₄CF₃)₄]⁻ | [(C₁₂H₂₅-Φ)₂I]⁺,[B(C₆F₅)₄]⁻ |
| [(Φ)₃S]⁺, [B(C₆F₄OCF₃)₄]⁻ | [(Φ-CH₃)₂I]⁺, [B(C₆F₅)₄]⁻ |
| [(Φ-CH₃)₂I]⁺, [B(C₆F₄OCF₃)₄]⁻ | [CH₃-Φ-I-Φ-CH(CH₃)₂]⁺, [B(C₆F₅)₄]⁻ |

(η⁵-cyclopentadienyl)(η⁶-toluene) Fe⁺, [B(C₆F₅)₄]⁻
(η⁵-cyclopentadienyl)(η⁶-methyl-1-naphthalene) Fe⁺, [B(C₆F₅)₄]⁻
(η⁵-cyclopentadienyl)(η⁶-cumene) Fe⁺, [B(C₆F₅)₄]³¹

As another literary reference for defining the onium borates (1) and (2) and the borates of organometallic salts (4), there may be mentioned the entire content of patent applications EP 0 562 897 and 0 562 922. This content is integrally incorporated by reference into the present disclosure.

As another example of onium salt which can be used as photoinitiator, there may be mentioned those disclosed in American patents U.S. Pat. Nos. 4,138,255 and 4,310,469.

Other cationic photoinitiators may also be used, e.g.:
those marketed by Union-Carbide (photoinitiator 6990 and 6974 triarylsulfonium hexafluorophosphate and hexafluoroantimonate),
the salts of iodonium hexafluorophosphate or hexafluoroantimonate,
or the ferrocenium salts of these various anions.

The nature of the photosensitizer contained in the dental composition according to the invention may be highly varied. In the context of the invention, it corresponds in particular to one of the following formulae (IV) to (XXII):

• formula (IV)

in which:
when n=1, Ar¹ represents an aryl radical containing from 6 to 18 carbon atoms, a tetrahydronaphthyl, thienyl, pyridyl or furyl radical or a phenyl radical carrying one or more substituents chosen from the group consisting of F, Cl, Br, CN, OH, linear or branched C₁-C₁₂ alkyls, —CF³, —OR⁶, —OPhenyl, —SR⁶, —SPhenyl, —SO₂Phenyl, —COOR⁶, —O—(CH₂—CH═CH₂), —O(CH₂H₄—O)ₘ—H, —O(C₃H₆O)ₘ—H, m being between 1 and 100, when n=2, Ar₁ represents a C₆-C₁₂ arylene radical or a phenylene-T-phenylene radical where T represents —O—, —S—, —SO₂— or —CH₂—, X represents a group —OR⁷ or —OSiR⁸(R⁹)₂ or forms, with R⁴, a group —O—CH(R¹⁰)—, R₄ represents a linear or branched C₁-C₈ alkyl radical which is unsubstituted or which carries an —OH, —OR⁶, C₂-C₈ acyloxy, —CF³ or —CN group, a C₃ or C₄ alkenyl radical, a C₆ to C₁₈ aryl radical, a C₇ to C₉ phenylalkyl radical, R⁵ has one of the meanings given for R⁴ or represents a radical —CH₂CH₂R¹¹, or alternatively forms with R⁴ a C₂-C₈ alkylene radical or a C₃-C₉ oxa-alkylene or aza-alkylene radical, R⁶ represents a lower alkyl radical containing from 1 to 12 carbon atoms, R⁷ represents a hydrogen atom, a C₁-C₁₂ alkyl radical, a C₂-C₆ alkyl radical carrying an —OH, —OR⁶ or —CN group, a C₃-C₆ alkenyl radical, a cyclohexyl or benzyl radical, a phenyl radical optionally substituted with a chlorine atom or a linear or branched C₁-C₁₂ alkyl radical, or a 2-tetrahydropyranyl radical, R⁸ and R⁹ are identical or different and each represent a C₁-C₄ alkyl radical or a phenyl radical, R¹⁰ represents a hydrogen atom, a C₁-C₈ alkyl radical or a phenyl radical, R¹¹ represents a radical —CONH₂, —CONHR⁶, —CON(R⁶)₂, —P(O)(OR⁶)₂ or 2-pyridyl;

° formula (V)

in which:
Ar² has the same meaning as Ar¹ of formula (IV) in the case where n=1, R¹⁵ represents a radical chosen from the group consisting of a radical Ar², a linear or branched C₁-C₁₂ alkyl radical, a C₆-C₁₂ cycloalkyl radical, and a cycloalkyl radical forming a C₆-C₁₂ ring with the carbon of the ketone or a carbon of the radical Ar², it being possible for these radicals to be substituted with one or more substituents chosen from the group consisting of —F, —Cl, —Br, —CN, —OH, —CF$_3$, —OR$^6$, —SR$^6$, —COOR$^6$, the linear or branched C$_1$-C$_{12}$ alkyl radicals optionally carrying an —OH, —OR$^6$ and/or —CN group, and the linear or branched C$_1$-C$_8$ alkenyl radicals;

• formula (VI)

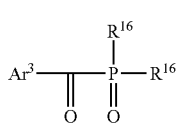

in which:
Ar$^3$ has the same meaning as Ar$^1$ of formula (IV) in the case where n=1,
R$^{16}$, identical or different, represents a radical chosen from the group consisting of a radical Ar$^3$, a radical —(C=O)—Ar$^3$, a linear or branched C$_1$-C$_{12}$ alkyl radical, a C$_6$-C$_{12}$ cycloalkyl radical, it being possible for these radicals to be substituted with one or more substituents chosen from the group consisting of —F, —Cl, —Br, —CN, —OH, —CF$_3$, —OR$^6$, —SR$^6$, —COOR$^6$, the linear or branched C$_1$-C$_{12}$ alkyl radicals optionally carrying an —OH, —OR$^6$ and/or —CN group, and the linear or branched C$_1$-C$_8$ alkenyl radicals;

formula (VII)

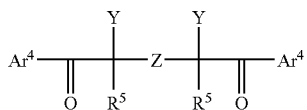

in which:
R$^5$, which are identical or different, have the same meanings as in formula (III),
Y, which are identical or different, represent X and/or R$^4$,
Z represents:
a direct bond,
a C$_1$-C$_6$ divalent alkylene radical, or a phenylene, diphenylene or phenylene-T-phenylene radical, or alternatively forms, with the two substituents R$^5$ and the two carbon atoms carrying these substituents, a cyclopentane or cyclohexane nucleus,
a divalent group —O—R$^{12}$—O—, —O—SiR$^8$R$^9$—O—SiR$^8$R$^9$—O—, or —O—SiR$^8$R$^9$—O—,
R$^{12}$ represents a C$_2$-C$_8$ alkylene, C$_4$-C$_6$ alkenylene or xylylene radical, and Ar$^4$ has the same meaning as Ar$^1$ of formula (IV) in the case where n=1.
family of thioxanthones of formula (VIII):

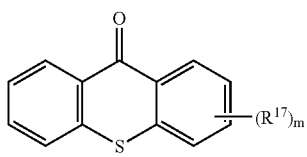

m=0 to 8,
R$^{17}$, identical or different substituent(s) on the aromatic nucleus (nuclei), represent a linear or branched C1-C12 alkyl radical, a C6-C12 cycloalkyl radical, a radical Ar$^1$, a halogen atom, an —OH, —CN, —NO$_2$, —COOR$^6$, —CHO, Ophenyl, —CF$_3$, —SR$^6$, —Sphenyl, —SO$_2$phenyl, Oalkenyl, or —SiR$^6{}_3$ group.

family of xanthenes of formula (IX):

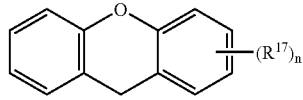

n=0 to 8
family of xanthones of formula (X):

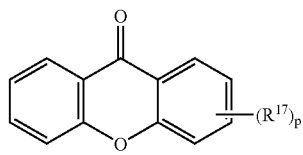

p=0 to 8
family of the naphthalene of formula (XI):

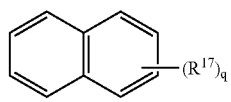

q=0 to 8
family of the anthracene of formula (XII):

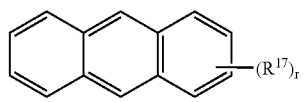

r=0 to 10
family of the phenanthrene of formula (XIII):

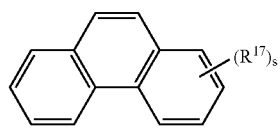

s=0 to 10
family of the pyrene of formula (XIV):

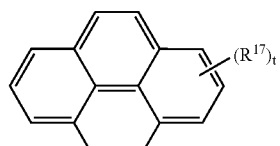

t=0 to 10
family of the fluorene of formula (XV):

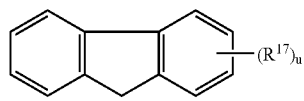

u=0 to 9 family of the fluoranthene of formula (XVI):

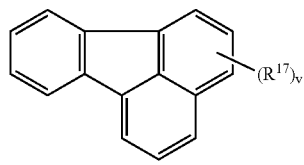

v=0 to 10 family of the chrysene of formula (XVII):

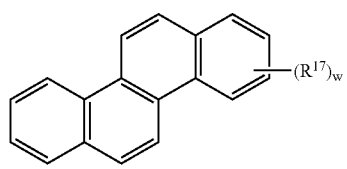

w=0 to 12 family of the fluorene of formula (XVIII):

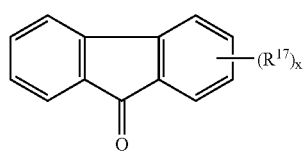

with x=0 to 8, for example 2,7-dinitro-9-fluorenone, family of the chromone of formula (XIX):

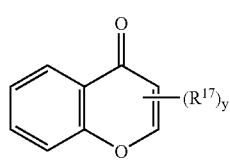

with y=0 to 6 family of the eosin of formula (XX):

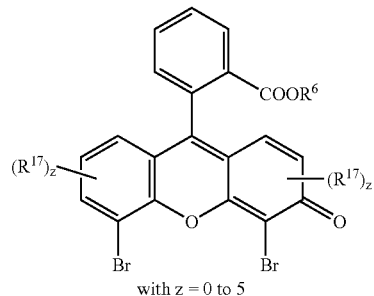

with z = 0 to 5

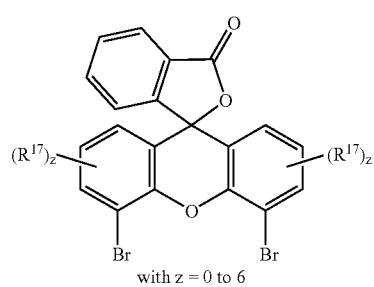

with z = 0 to 6 family of the erythrosin of formula (XXI):

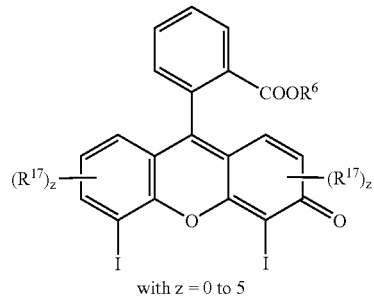

with z = 0 to 5

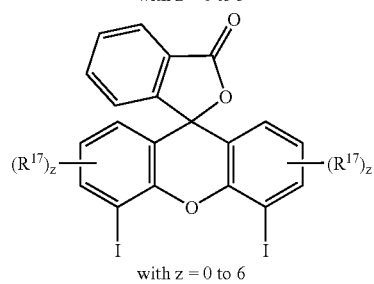

with z = 0 to 6 family of the biscoumarins of formula (XXII):

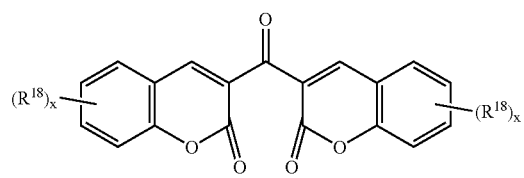

R[18], identical or different, has the same meaning as R[17] or represents a group —NR[6]$_2$, for example 3,3'-carbonylbis(7-diethylaminocoumarin) and 3,3'-carbonyl-bis(7-methoxycoumarin).

Other sensitizers can be used. In particular, the photosensitizers described in the documents U.S. Pat. Nos. 4,939,069; 4,278,751; 4,147,552 may be used.

In the context of the present invention, the photosensitizers have a residual absorption of UV light between 200 and 500 nm, preferably 400 to 500 nm for the preparations of dental prostheses. For dental restoration, a photosensitizer having a residual absorption of UV light above 400 nm will be preferred.

According to a preferred variant, the photosensitizers will be chosen from those of the families (IV), (VII) and (VIII). By way of examples, the following photosensitizers will be mentioned:

4,4'-dimethoxybenzoin; 2-4-diethylthioxanthone
2-ethylanthraquinone; 2-methylanthraquinone;
1,8-dihydroxyanthraquinone; dibenzoylperoxide;
2,2-dimethoxy-2-phenylacetophenone; benzoin;
2-hydroxy-2-methylpropiophenone; benzaldehyde;
4-(2-hydroxyethoxy)phenyl-(2-hydroxy-2-methylpropyl)-ketone;
benzoylacetone;

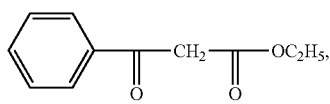

2-isopropylthioxanthone; 1-chloro-4-propoxy-thioxanthone;
4-isopropylthioxanthone; and the mixture thereof.

Various types of fillers can be used for preparing the compositions according to the invention. The fillers are chosen according to the final use of the dental composition: these affect important properties such as appearance, penetration of UV radiation, as well as the mechanical and physical properties of the material obtained after crosslinking and/or polymerization of the dental composition.

As reinforcing filler, there may be used treated or untreated pyrogenic silica fillers, amorphous silica fillers, quartz, glass or nonglassy fillers based on oxides of zirconium, barium, calcium, fluorine, aluminum, titanium, zinc, borosilicates, aluminosilicates, talc, spherosil, yterbium trifluoride, fillers based on polymers in ground powder form, such as inert or functionalized methyl polymethacrylates, polyepoxides or polycarbonates.

By way of example, there may be mentioned:
inert fillers based on methyl polymethacrylate LUXAS-ELF from the company UGL, which can be used in the dental field and which are pigmented in pink,
hexamethyldisilazane-treated fumed silica fillers having a specific surface area of 200 m$^2$/g,
untreated fumed silica fillers ("aerosil" AE200 marketed by DEGUSSA).

According to an advantageous variant of the invention, the fillers and in particular the silica fillers are treated before use at 120° C. with a quantity of less than 10% w/w of silicone comprising at least one unit of formula (XXIII):

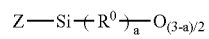

such that Z' has the same definition as Z–a=0,1,2 or 3 with at least one silicon atom.

There may be mentioned by way of example the polymer described below with Z=epoxide and Z=trialkoxysilyl

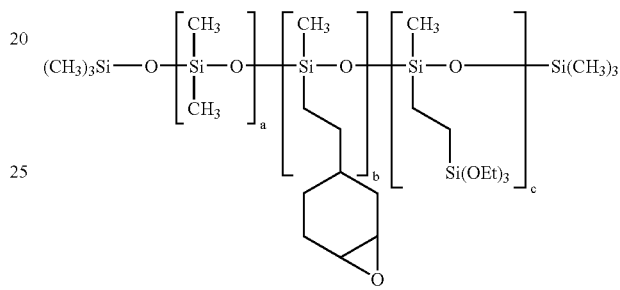

a = 9; b = 2; c = 2

In this case for the treatment of silicone-containing filler(s), in particular silica, with this type of polymer, the material obtained after crosslinking has a mechanical strength, a modulus of elasticity and a resistance to compression which are markedly improved.

In addition to the reinforcing fillers, pigments may be used to color the dental composition according to the invention envisaged and the ethnic groups.

For example, red pigments are used in the presence of microfibers for the dental compositions used for the preparation of dental prostheses in order to simulate the blood vessels.

Pigments based on metal oxides (iron and/or titanium and/or aluminum and/or zirconium oxides, and the like) are also used for the dental compositions used for the preparation of restoration material, in order to obtain a crosslinked material having an ivory color.

Other additives may be incorporated into the dental compositions according to the invention. For example, biocides, stabilizers, flavoring agents, plasticizers and adherence promoters.

Among the additives which may be envisaged, there will be advantageously used crosslinkable and/or polymerizable coreagents of the organic type. These coreagents are liquid at room temperature or are hot-meltable at a temperature of less than 100° C., and each coreagent comprises at least two reactive functional groups such as oxetane-alkoxy, oxetane-hydroxyl, oxetane-alkoxysilyl, carboxyl-oxetane, oxetane-oxetane, alkenyl ether-hydroxyl, alkenyl ether-alkoxysilyl, epoxy-alkoxy, epoxy-alkoxysilyls, dioxolane-dioxolane-alcohol, and the like.

The dental compositions according to the invention may be used for numerous dental applications, and in particular in the field of dental prostheses, in the field of dental restoration and in the field of temporary teeth.

The dental composition according to the invention is preferably provided in the form of a single product containing the various components ("monocomponent") which facilitates its use, in particular in the field of dental prostheses. Optionally, the stability of this product may be provided for by organic derivatives with amine functional groups according to the teaching of the document WO 98/07798.

In the field of dental prostheses, the product in the "monocomponent" form may be deposited with the aid of a syringe directly on the plaster model or in a core. Next, it is polymerized (polymerization by possible successive layers) with the aid of a UV lamp (visible light spectrum 200-500 nm).

In general, it is possible to produce a lasting and esthetic dental prosthesis in 10 to 15 min.

It should be noted that the products obtained from the dental composition according to the invention are nonporous. Thus, after an optional polishing with the aid of a felt brush, for example, the surface of the dental prostheses obtained is smooth and bright and therefore does not require the use of varnish.

The applications in the field of dental prostheses are essentially those of the joined prosthesis, which can be divided into two types:
  full prosthesis in the case of a patient with absolutely no teeth
  partial prosthesis due to the absence of several teeth, resulting either in a provisional prosthesis, or a skeleton brace.

In the field of dental restoration, the dental composition according to the invention may be used as material for filling the anterior and posterior teeth in different colors (for example "VITA" colors), which is rapid and easy to use.

The dental composition being nontoxic and polymerizable in thick layers, it is not essential to polymerize the material in successive layers. In general, a single injection of the dental composition is sufficient.

The preparations for dental prostheses and for restoration materials are carried out according to techniques which are customary in the art.

In the case of application of the dental composition as a tooth, either the tooth may be pretreated with a bonding primer or the dental composition may be prepared as a mixture with a bonding primer before its use. However, it is not essential to use a bonding primer in order to use the dental composition according to the invention.

The following examples and tests are given by way of illustration. They make it possible in particular to understand more clearly the invention and to highlight some of its advantages and to illustrate a few of its variant embodiments.

EXAMPLES AND TESTS

The product used in the compositions of the examples are the following:

product (A):

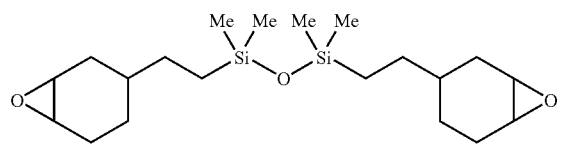

Product (B): this product is a mixture of siloxanes, whose viscosity is 23.5 mPa.s and in which the proportions by weight and formulae $B_1$, $B_2$ and $B_3$ are given below:

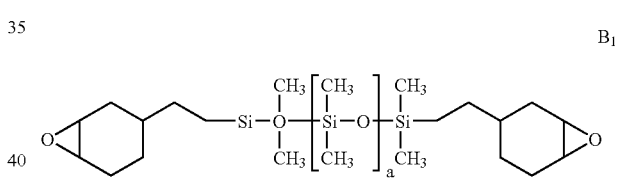

with 89% of $B_1$ where a=0, 9% of $B_1$ where a=1; 0.2% of $B_1$ where a=2;

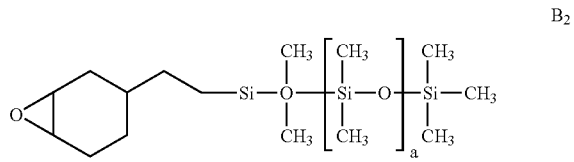

with 0.3% of B2 where a=0;

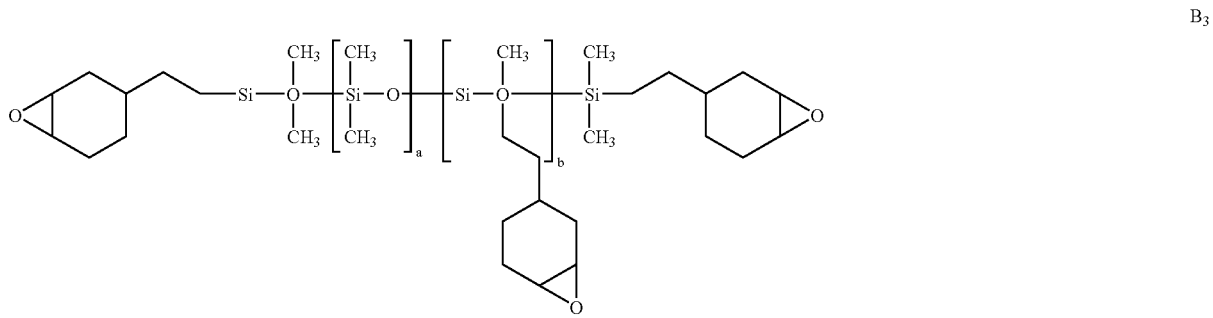

B₃ and with 1.5% of B3 where a=0 and b=1.

product (P1):

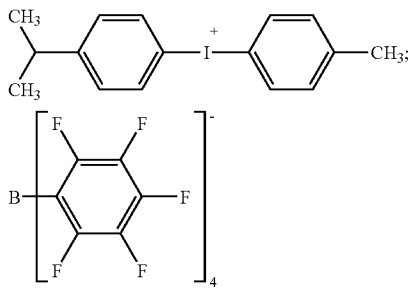

Product (PSI): Isopropylthioxanthone Marketed Under the Trademark Quantacure ITX by the Company RAHN.

Example 1

Composition for Dental Prosthesis

The following are mixed using a three-blade stirrer:
100 parts of siloxane (A) stabilized with 50 ppm of Tinuvin 765;
1 part of photoinitiator (P1) at 75% in ethyl acetate;
0.028 part of photosensitizer (PS1);
150 parts of a pink-pigmented, polymethyl methacrylate-based inert filler (product LUXASELF from UGL dentaire).

The composition obtained is perfectly stable in the absence of light for several months at room temperature. This composition can be worked manually and for several hours in the presence of daylight.

A test piece 2.8±0.3 mm thick is prepared in a glass dish 64 mm long (model), 10 mm wide (model) and open at the top by pouring the prepared composition ("monocomponent") into the dish.

The composition is dried by passing-the dish for 1 to 2 seconds (3 m/min) under a UV lamp of 200 W/cm power corresponding to the excitation of a mixture of mercury and gallium and emitting in the UV-visible range above 400 nm.

The product obtained is unmolded by breaking the glass.

The SHORE D hardness of the two polymerized compositions is determined on each side of the item made immediately after crosslinking.

| Example 1 | Immediate measurement | Measurement after 10 hours |
|---|---|---|
| Irradiated surface: | 70 | 85 |
| Bottom surface | 60 | 85 |

The Shore D hardness continues to change substantially over a few hours.

The volume shrinkage is very low and excellent size stability is obtained.

The loss of mass is less than 1%.

The product may be used with or without bonding primer in the presence of artificial teeth or of natural teeth.

More generally, the properties of the material obtained are in agreement with the DIN/ISO 1567 standard.

Example 2

Composition for Dental Restoration

A composition for dental restoration is prepared by mixing:
200 parts of siloxane (A) stabilized with 50 ppm of Tinuvin 765;
1.8 parts of photoinitiator (P1) at 75% in ethyl acetate;
0.0178 part of photosensitizer (PS1);
52 parts of hexamethyldisilazane-treated fumed silica having a specific surface area of 200 m²/g;
20 parts of untreated amorphous silica dried for 4 hours at 200° C. before formulation.

A flowing composition is obtained which has a translucent gray appearance.

The crosslinking-polymerization operation is carried out using a lamp emitting a light spot emitted through a curved light tip 8 mm in diameter. The source is an Optibulb 80 W lamp (DEMETRON Optilux 500) for wavelengths of between 400 and 520 nm.

The dental composition is applied in a tooth. A thickness of 5 mm is crosslinked in less than 30 seconds.

A SHORE D hardness of 50 is obtained immediately and can reach 80 to 100 within a few hours.

No loss is observed in size stability. The porosity of the crosslinked material, based on observation of a section under a microscope, is zero.

The color of the composite after crosslinking is close to ivory color.

Example 3

Composition for Dental Restoration

The same concentrations of components and the same procedure as above in Example 2 are used.

However, the mixture of fillers is treated, before use, at 120° C. with 5% w/w of silicone of average general formula containing less than 50 ppm of residual platinum:

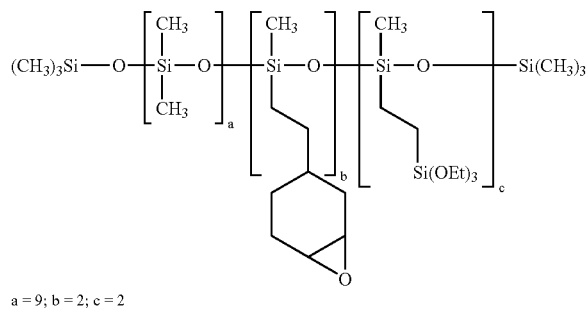

a = 9; b = 2; c = 2

The restoration material obtained after crosslinking according to the procedure of Example 2 has a better mechanical strength, an improved modulus of elasticity and a better compression resistance.

A SHORE D hardness of 80 is obtained immediately.

The size stability and the porosity properties of the material are excellent.

Example 4

Dental Precomposition

A dental precomposition, prepared without fillers, is obtained by mixing using a magnetic stirrer bar:
- 1 part of siloxane (A) having a density of 0.997, stabilized with 50 ppm of Tinuvin 765,
- 0.01 part of photoinitiator (P1) at 10% in solution, dissolved directly in siloxane A,
- 0.00028 part of photosensitizer (PS1) contained in the photoinitiator (P1).

The crosslinking operation is carried out in a manner identical to that of Example 2. A composition 5 mm thick is crosslinked in less than 30 seconds.

The density of the crosslinked composition is measured using a brass pycnometer and its value is 1.0274. The volume shrinkage is therefore 3.05% [=(1.0274−0.997)/0.997×100] in the absence of fillers. Consequently, a dental composition of this type, formulated with more than 50% of filler, will have a very low volume shrinkage which is less than 1.5%.

Example 5

Dental Precomposition (a) A dental precomposition prepared without fillers is obtained by mixing using a three-blade stirrer,
- 10 parts of siloxane (A) having a density of 0.997, stabilized with 50 ppm of Tinuvin 765,
- 0.01 part of photoinitiator (P1) dissolved directly in silicone (A),
- and 62 ppm of photosensitizer (PS1) contained in the photoinitiator.

Eight grams of this dental precomposition are then placed in an open cylindrical aluminum cup in a manner such that the volume occupied represents a thickness of about 6 mm.

The liquid is photocrosslinked by passing the cup under a UV lamp delivering, through a pane of glass 6 mm thick, UV-V (>390 nm)=0.6 W/cm$^2$. The UV-V (>390 nm) dose received is 0.4 J/cm$^2$ at 10 m/min.

The degree of conversion of the epoxy functional groups immediately after polymerization is measured from the residual heat of reaction recorded by differential calorimetry. The residual heat is 17 J/g relative to a noncrosslinked sample which represents 237 J/g. The effective degree of conversion of the epoxy functional groups with 0.1% photoinitiator is therefore 93%.

(b) The same composition as above in (a) is prepared by adding 5% w/w of 3-ethyl-3-(hydroxymethyl)oxetane during the preparation of the composition. The composition is then crosslinked in the same manner as above in (a).

The degree of conversion of the epoxy functional groups is 99.3% with a residual heat of 1.5 J/g.

(c) The same composition as above in (a) is prepared by adding 10% w/w of 3-ethyl-3-(hydroxymethyl)oxetane during the preparation of the composition. The composition is then crosslinked in the same manner as above in (a).

The degree of conversion of the epoxy functional groups is 99.95% with a residual heat of 0.1 J/g.

Example 6

Composition for Dental Prosthesis or Dental Restoration Material

The following are mixed using a three-blade stirrer:
- 95 parts of siloxane (A) stabilized with 50 ppm of Tinuvin 765,
- 62 ppm of photosensitizer (PS1),
- 0.5 part of photoinitiator (P1) at 10% in siloxane (A),
- 5 parts of 3-ethyl-3-(hydroxymethyl)-oxetane,
- and 120 parts of precipitated silica (ground quartz).

A dental composition is obtained with is opaque, gray in color, nonflowing and easy to handle.

The crosslinking operation is carried out in a manner identical to that of Example 2. A composition 5 mm thick crosslinks in less than 30 seconds.

The color of the material after crosslinking is close to ivory color.

The material is suitable in particular for dental prosthesis use, in particular the stiffness is greater than 80 Mpa according to the ISO 1567 standard.

Example 7

Dental Composition

This composition is formulated with:
- 95 parts of silicone (B), 62 ppm of photosensitizer (PS1),
0.5 part of photoinitiator (P1) at 10% in siloxane (B),
5 parts of the oxetane 3-ethyl-3-(hydroxymethyl)oxetane,
and 120 parts of precipitated silica (ground quartz).

The crosslinking operation is carried out in a manner identical to that of Example 2.

The stiffness values found are greater than 80 Mpa according to the ISO 1567 standard.

Example 8

Dental Precomposition

A dental precomposition M1 prepared without fillers is obtained by mixing using a three-blade stirrer:
 100 parts of a silicone composition (B) having a density of 0.997 and stabilized with 50 ppm of Tinuvin 765,
 0.1 part of photoinitiator (P1) at 10% in solution, dissolved directly in silicone (B),
 and 0.028 part of photosensitizer (PS1).

A portion of the composition obtained M1 is removed so as to crosslink it. The crosslinking operation is carried out in a manner identical to that of Example 2. A composition 5 mm thick crosslinks in less than 30 seconds.

The density of the crosslinked material, measured using a brass pycnometer, is 1.0274. The volume shrinkage is therefore 3.05% [=(1.0274−0.997)/0.997×100] in the absence of fillers. Consequently, a dental composition of this type, formulated with more than 50% of fillers, will have a very low volume shrinkage which is less than 1%.

Example 9

Dental Precomposition (a) Eight grams of M1 of Example 8 are placed in an open cylindrical aluminum cup such that the volume occupied represents a thickness of about 6 mm.

The photocrosslinking of M1 and the calculation of the degree of conversion of the epoxy functional groups are carried out according to the methods described in Example 5.

The residual heat is 17 J/g.relative to a noncrosslinked sample which represents 237 J/g. Consequently, the effective degree of conversion of the epoxy functional groups with 0.1% of photoinitiator is therefore 93%.

(b) The photocrosslinking and the calculation of the degree of conversion of the epoxy functional groups are also carried out for a composition M1 containing 5% w/w of a silicone oil of formula $B_1$ with a=12 on average.

The degree of conversion of the epoxy functional groups is 99% with a residual heat of 1.5 J/g.

(c) The photocrosslinking and the calculation of the degree of conversion of the epoxy functional groups are also carried out for a composition M1 containing 5% w/w of a silicone oil with a=12 on average and of formula:

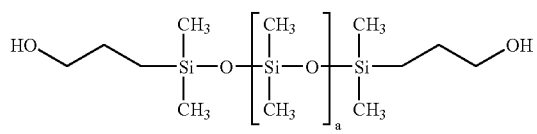

The degree of conversion of the epoxy functional groups is 99% with a residual heat of 0.1 J/g.

(d) The photocrosslinking and the calculation of the degree of conversion of the epoxy functional groups are also carried out for a composition M1 containing 5% by weight of siloxane resin of the $MQM^{Epoxy}$ type containing 0.5% by weight of hydroxysilyl functional groups and 2% by weight of epoxy functional group (mass 43).

The degree of conversion of the epoxy functional groups is 99%.

Example 10

Composition for Dental Prosthesis or Dental Restoration Material

The following are mixed using a three-blade stirrer:
 100 parts of silicone (B),
 62 ppm of photosensitizer (PS1),
 0.5 part of photoinitiator (P1) at 10% in solution in silicone (B),
 and 120 parts of precipitated silica (ground quartz).

A mixture is obtained which is opaque, gray in color, nonflowing and capable of being handled.

The crosslinking operation is carried out in a manner identical to that of Example 2. A composition 5 mm thick is crosslinked in less than 30 seconds. The color of the material after crosslinking is similar to ivory color.

The composition, in this case, is suitable in particular for dental prostheses, in particular the stiffness is greater than 80 Mpa according to the ISO 1567 standard.

Example 11

Dental Composition

The following are mixed using a three-blade stirrer:
 95 parts of silicone (B) stabilized with 50 ppm of Tinuvin 765,
 62. ppm of photosensitizer (PS1),
 0.5 part of photoinitiator (P1) at 10% in silicone (B),
 5 parts of polydimethylsiloxane B1 where a=12 on average,
 and 120 parts of precipitated silica (ground quartz).

The crosslinking operation is carried out in a manner identical to that of Example 2. The measured stiffness values are greater than 80 Mpa according to the ISO 1567 standard.

The invention claimed is:

1. A process for the preparation of a dental prosthesis or dental restoration, comprising the step of shaping and curing a low shrinking polymerizable or crosslinkable dental composition comprising a mixture of:
 (1) at least one crosslinkable and/or polymerizable silicone oligomer or polymer which is liquid at room temperature or which is heat-meltable at a temperature of less than 100° C., and which comprises:
  at least one unit of formula (FS):

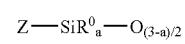

wherein:
   a=0.1 or 2,
   $R^0$, identical or different, represents an alkyl, cycloalkyl, aryl, vinyl, hydrogeno or alkoxy radical,
   Z, identical or different, is an organic substituent comprising at least one reactive epoxy, or alkenyl ether or oxetane or dioxolane or carbonate functional group,
   and at least two silicon atoms, (2) at least one aromatic hydrocarbon photosensitizer, having a residual light absorption of between 200 and 500 nm, and selected from the group consisting of the following formulae (VIII), (X). (XII) and (XXII):

thioxanthones of formula (VIII):

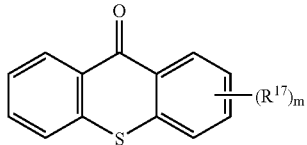

wherein:

m=0 to 8, $R^{17}$, identical or different substituent(s) on the aromatic nucleus (nuclei), represent a linear C1-C12 alkyl radical, a branched C1-C12 alkyl radical, a C6-C12 cycloalkyl radical, a radical $Ar^1$, a halogen atom, an —OH, —CN, —NO$_2$, —COOR$^6$, —CHO, Ophenyl, —CF$_3$, —SR$^6$, —Sphenyl, —SO$_2$phenyl, Oalkenyl, or —SiR$^6{}_3$ group;

xanthones of formula (X):

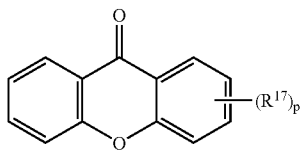

wherein p=0 to 8 anthracene of formula (XII):

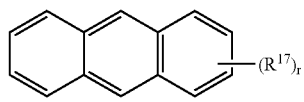

wherein=0 to 10, and biscoumarins of formula (XXII):

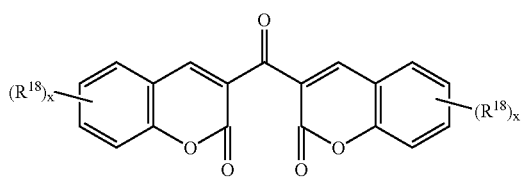

wherein:

$R^{18}$, identical or different, has the same meaning as $R^{17}$ above or represents a group:

—NR$^6{}_2$, wherein R$_6$ represents a linear C1-C12 alkyl radical, (3) at least one dental filler present in a proportion of at least 10% by weight relative to the total weight of the composition, and (4) an effective quantity of at least one borate-type photoinitiator, whose borate residue is:

| | |
|---|---|
| 1': | [B(C$_6$F$_5$)$_4$]$^-$ |
| 2': | [(C$_6$F$_5$)$_2$BF$_2$]$^-$ |
| 3': | [B(C$_6$H$_4$CF$_3$)$_4$]$^-$ |
| 4': | [B(C$_6$F$_4$OCF$_3$)$_4$]$^-$ |
| 5': | [B(C$_6$H$_3$(CF$_3$)$_2$)$_4$]$^-$ |
| 6': | [B(C$_6$H$_3$F$_2$)$_4$]$^-$ |
| 7': | [C$_6$F$_5$BF$_3$]$^-$ | wherein the cationic entity of the borate is:

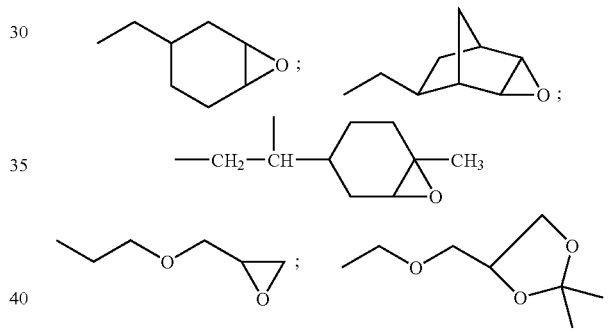

and wherein the composition has a volumetric polymerization and/or crosslinking shrinkage of less than 1.5% v/v.

2. The process as claimed in claim 1, wherein Z is an organic substituent Z1 comprising at least one reactive epoxy, or dioxolane functional group.

3. The process as claimed claim 1, wherein the reactive functional group Z1 is:

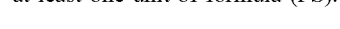

4. A process for the preparation of a dental prosthesis or dental restoration, comprising the step of shaping and curing a low shrinking polymerizable or crosslinkable dental composition comprising a mixture of:

(1) at least one crosslinkable and/or polymerizable silicone oligomer or polymer which is liquid at room temperature or which is heat-meltable at a temperature of less than 100° C., and which comprises:

at least one unit of formula (FS):

$$Z\text{—SiR}_a{}^0\text{—O}_{(3-a)/2}$$

wherein:

a=0,1 or 2, $R^0$, identical or different, represents an alkyl, cycloalkyl, aryl, vinyl, hydrogeno or alkoxy radical, Z, identical or different, is an organic substituent comprising at least one reactive epoxy, or alkenyl ether or oxetane or dioxolane or carbonate functional group, and at least two silicon atoms, (2) at least one aromatic hydrocarbon photosensitizer, and (4) an effective quantity of at least one borate-type photoinitiator, whose borate residue is:

| | |
|---|---|
| 1': | $[B(C_6F_5)_4]^-$ |
| 2': | $[(C_6F_5)_2BF_2]^-$ |
| 3': | $[B(C_6H_4CF_3)_4]^-$ |
| 4': | $[B(C_6F_4OCF_3)_4]^-$ |
| 5': | $[B(C_6H_3(CF_3)_2)_4]^-$ |
| 6': | $[B(C_6H_3F_2)_4]^-$ |
| 7': | $[C_6F_5BF_3]^-$ | wherein the cationic entity of the borate is:

| | | |
|---|---|---|
| $[(\Phi)_2I]^+$ | $[C_8H_{17}\text{—}O\text{-}\Phi\text{-}I\text{-}\Phi]^+$ | $[(\Phi\text{-}CH_3)_2I]^+$ |
| $[C_{12}H_{25}\text{-}\Phi\text{-}I\text{-}\Phi]^+$ | $[(C_8H_{17}\text{—}O\text{-}\Phi)_2I]^+$ | $[(C_8H_{17}\text{—}O\text{-}\Phi\text{-}I\text{-}\Phi)]^+$ |
| $[(\Phi)_3S]^+$ | $[(\Phi)_2\text{-}S\text{-}\Phi\text{-}O\text{—}C_8H_{17}]^+$ | $[(CH_3\text{-}\Phi\text{-}I\text{-}\Phi\text{-}CH(CH_3)_2]^+$ |
| $[\Phi\text{-}S\text{-}\Phi\text{-}S\text{-}(\Phi)_2]^+$ | $[(C_{12}H_{25}\text{-}\Phi)_2I]^+$ | $[(CH_3\text{-}\Phi\text{-}I\text{-}\Phi\text{-}OC_2H_5]^+$ | wherein the composition has a volumetric polymerization and/or crosslinking shrinkage of less than 1.5% v/v. and wherein the photosensitizer is 3,3'-carbonylbis(7-diethylaminocoumarin) or 3,3'-carbonylbis(7-methoxycoumarin).

5. The process as claimed in claim 4, wherein Z is an organic substituent Z1 comprising at least one reactive epoxy, or dioxolane functional group.

6. The process as claimed claim 4, wherein the reactive functional group Z1 is:

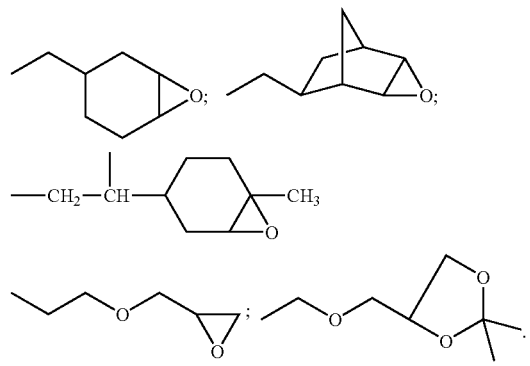

* * * * *